United States Patent [19]

Bigg

[11] 4,349,557
[45] Sep. 14, 1982

[54] THIAZOLE DERIVATIVES AND PHARMACEUTICAL COMPOSITIONS CONTAINING THEM

[75] Inventor: Dennis Bigg, Jouy en Josas, France

[73] Assignee: Synthelabo, Paris, France

[21] Appl. No.: 251,744

[22] Filed: Apr. 7, 1981

[30] Foreign Application Priority Data

Apr. 8, 1980 [FR] France .................................. 80 07845

[51] Int. Cl.$^3$ ........................................... C07D 277/60
[52] U.S. Cl. .................................... 424/270; 548/154; 548/337
[58] Field of Search ................. 548/154, 155; 424/270

[56] References Cited

U.S. PATENT DOCUMENTS 3,806,515 4/1974 Houlihan et al. .................... 548/154
4,110,460 8/1978 Baetz ...................................... 548/154
4,282,225 8/1981 Bigg ...................................... 548/155

Primary Examiner—Nicholas S. Rizzo
Attorney, Agent, or Firm—Wegner & Bretschneider

[57] ABSTRACT

Thiazole derivatives of the general formula:

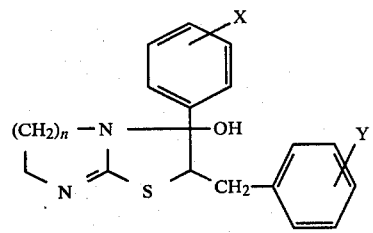

wherein n represents 1 or 2 and each of X and Y independently of one another represents one or more substituents selected from hydrogen and halogen atoms, the trifluoromethyl radical and straight- or branched-chain alkyl and alkoxy radicals of 1 to 4 carbon atoms, are new therapeutically useful compounds, especially of interest in the treatment of depression.

9 Claims, No Drawings

THIAZOLE DERIVATIVES AND PHARMACEUTICAL COMPOSITIONS CONTAINING THEM

The present invention relates to new therapeutically useful thiazole derivatives, processes for their preparation, pharmaceutical compositions containing them and their use in therapy.

The thiazole derivatives of the present invention are those compounds of the general formula:

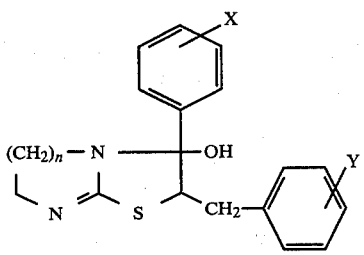

wherein n represents 1 or 2 and each of X and Y independently of one another represents one or more substituents selected from hydrogen and halogen atoms, the trifluoromethyl radical and straight- or branched-chain alkyl and alkoxy radicals of one to four carbon atoms, and pharmaceutically acceptable acid addition salts thereof.

The thiazole derivatives of general formula I can also exist in the following open form:

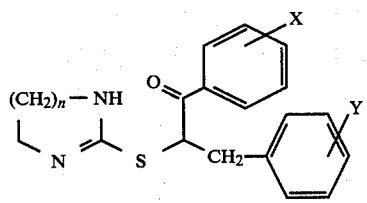

wherein X, Y and n are as hereinbefore defined.

The compounds of general formula I possess a centre of asymmetry and can exist in the form of racemates or enantiomers. The present invention includes the enantiomers and mixtures, particularly racemates, thereof.

Preferred compounds of the present invention are those of general formula I wherein n is 1 and, more particularly, those wherein each of X and Y independently of one another represents one or more hydrogen or halogen atoms, or trifluoromethyl, methyl, tert.-butyl or methoxy radicals; or n is 2 and, more particularly, those compounds wherein each of X and Y independently of one another represents one or more hydrogen or halogen atoms, or methyl, methoxy, tert.-butyl, n-butoxy or n-propoxy radicals. Of outstanding importance are 2-benzyl-3-(3,4-dichlorophenyl)-2,3,5,6-tetrahydroimidazo[2,1-b]thiazol-3-ol and 2-benzyl-3-(4-bromophenyl)-2,3,5,6-tetrahydroimidazo[2,1-b]thiazol-3-ol, and their pharmaceutically acceptable acid addition salts.

According to a feature of the present invention, the thiazole derivatives of general formula I are prepared by the process which comprises reacting a ketone of the general formula:

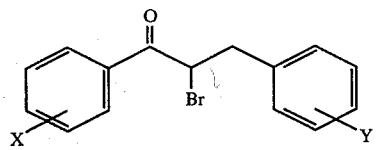

(wherein X and Y are as hereinbefore defined) with ethylene-thiourea or 3,4,5,6-tetrahydropyrimidine-2-thiol of the formulae IV and V respectively.

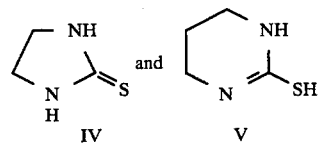

According to a further feature of the invention, the thiazole derivatives of general formula I are prepared by the process which comprises reacting a compound of the general formula:

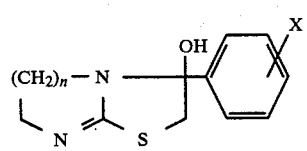

(wherein X and n are as hereinbefore defined) in the presence of sodium hydride with a benzyl halide of the general formula:

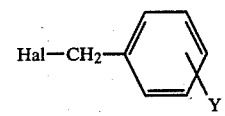

wherein Hal represents a halogen atom, e.g. bromine, and Y is as hereinbefore defined.

The thiazole products obtained by the first described method can be converted to a base of general formula I by reaction with a suitable base (for example $Na_2CO_3$ or $NaHCO_3$), and the thiazole products obtained by the second described method can be converted into pharmaceutically acceptable acid addition salts by methods known per se.

The reaction of a ketone of general formula III with ethylene-thiourea or 3,4,5,6-tetrahydropyrimidine-2-thiol is advantageously carried out in an inert organic solvent, for example acetone, at ambient temperature.

The reaction of a compound of general formula VI with a benzyl halide of general formula VII is advantageously carried out in the presence of an inert organic solvent, preferably dimethylformamide, in the presence of sodium hydride at ambient temperature.

The ketone starting materials of general formula III can be obtained either by the conventional reaction of the nitrile with the Grignard reagent, followed by hydrolysis, for example in accordance with the method described by W. K. Humphlett, M. J. Weiss and C. R. Hauser, J. Amer. Chem. Soc., 70, 4020 (1948), or by the reaction of the acid chloride with the Grignard reagent in tetrahydrofuran at −78° C., for example in accordance with the method described by F. Sato, M. Inoue, K. Oguro and M. Sata, Tetrahedron Letters No. 44, pages 4303–4306 (1979).

The starting materials of general formula VI can be prepared from the correspondingly substituted α-bromoacetophenone and ethylene-thiourea or 3,4,5,6-tetrahydropyrimidine-2-thiol, for example in accordance with the method described by Sharpe et al., Journal of Medicinal Chemistry, 1971, Volume 14, No. 10, pages 977–982.

The following Examples illustrate the preparation of thiazole derivatives of general formula I by the hereinbefore described processes.

The analyses and the IR and NMR spectra confirm the structure of the compounds.

EXAMPLE 1

2-Benzyl-3-(3-trifluoromethylphenyl)-2,3,5,6-tetrahydroimidazo[2,1-b]thiazol-3-ol

[n=1, X=3-CF$_3$, Y=]

2.24 g (0.022 mol) of ethylene-thiourea in 280 cc of acetone are introduced into a 1 liter Erlenmeyer flask and 9.88 g (0.0277 mol) of 3-trifluoromethyl)phenyl α-bromo-phenethyl ketone, dissolved in 70 cc of acetone, are added. The mixture is stirred for 20 hours and the white precipitate which appears is filtered off, washed with acetone, dried and recrystallised from methanol containing a small amount of chloroform. This yields a white solid which is dried in vacuo, at ambient temperature, in the presence of P$_2$O$_5$.

Melting point=169°–170° C.

The base is obtained in water by the addition of sodium bicarbonate and extraction with ethyl acetate. The ethyl acetate extract is washed with water and dried. It is evaporated in vacuo at 40° C. and the residue is taken up in diethyl ether. The resulting product is recrystallised from acetone. This yields a white solid.

Melting point=161°–163° C.

EXAMPLE 2

2-(4-Fluorobenzyl)-3-phenyl-2,3,5,6-tetrahydroimidazo[2,1-b]thiazol-3-ol

[n=1, X=H, Y=4-F]

9.85 g (0.032 mol) of α-bromo-4-fluoro-phenethyl phenyl ketone, dissolved in 80 cc of acetone, are added to 1.6 g (0.016 mol) of ethylene-thiourea, dissolved in 220 cc of acetone. The mixture is stirred for 20 hours and the white precipitate which appears is then filtered off, rinsed and dried. This yields the hydrobromide of the desired compound.

Melting point=177°–178° C.

This compound is taken up in a mixture of water and chloroform and the base is liberated by adding Na$_2$CO$_3$. The mixture is extracted with chloroform and the chloroform extract is washed with water, dried and concentrated. The residue is taken up in diethyl ether and this yields a white solid.

Melting point=169°–170° C.

EXAMPLE 3

2-Benzyl-3-(4-chlorophenyl)-2,3,5,6-tetrahydroimidazo[2,1-b]thiazol-3-ol

[n=1, X=4-Cl, Y=H]

6.3 g (0.145 mol) of 56% sodium hydride, which has been washed with petroleum ether, are introduced under argon into a 2 liter round-bottomed flask. 22.0 g (0.0865 mol) of 3-(4-chlorophenyl)-2,3,5,6-tetrahydroimidazo[2,1-b]thiazol-3-ol, dissolved in 300 cc of dimethylformamide are added. The mixture is stirred for 1 hour and 17.3 g (0.101 mol) of benzyl bromide, dissolved in 20 cc of dimethylformamide, are then added dropwise. After stirring for 1 hour, a precipitate forms. 400 cc of water and 500 cc of diethyl ether are added. A white solid is filtered off and washed with ethyl acetate and then with diethyl ether. It is recrystallised from a mixture of CHCl$_3$/CH$_3$OH/carbon black. This yields a white solid, which is dried at 60° C. over P$_2$O$_5$ in vacuo.

Melting point=172°–173.5° C.

EXAMPLE 4

2-(2-Methylbenzyl)-3-phenyl-2,3,5,6-tetrahydroimidazo[2,1-b]thiazol-3-ol

[n=1, X=H, Y=2-CH$_3$]

7.0 g (0.145 mol) of 50% sodium hydride, which has been washed with petroleum ether, are introduced under argon into a 2 liter round-bottomed flask. 19.06 g (0.0865 mol) of 3-phenyl-2,3,5,6-tetrahydroimidazo[2,1-b]thiazol-3-ol, dissolved in 300 cc of dimethylformamide, are added. The mixture is stirred for 1 hour and 18.7 g (0.101 mol) of α-bromo-o-xylene, dissolved in 30 cc of dimethylformamide, are then added dropwise. After 2 hours, 400 cc of water and 500 cc of diethyl ether are added to the reaction mixture. A solid forms. It is filtered off and rinsed with water and acetone and then with diethyl ether. This yields a beige solid which is recrystallised from a mixture of CHCl$_3$/CH$_3$OH/carbon black. This yields a white solid which is dried over P$_2$O$_5$, at ambient temperature, in vacuo.

Melting point=199°–201° C.

EXAMPLE 5

2-Benzyl-3-(2,4-dichlorophenyl)-2,3,6,7-tetrahydro-5H-thiazolo[3,2-a]pyrimidin-3-ol

[n=2, X=2, 4-Cl$_2$, Y=H]

In a 2 liter Erlenmeyer flask, 12.3 g (0.034 mol) of α-bromo-phenethyl 2,4-dichlorophenyl ketone, dissolved in 50 cc of acetone, are introduced into a solution of 3.72 g (0.032 mol) of 3,4,5,6-tetrahydropyrimidine-2-thiol in 1000 cc of acetone. The mixture is stirred for 24 hours. This yields a white solid which is filtered off, rinsed and dried.

Melting point=241°–242° C.

The base is liberated from its salt, in a mixture of water and chloroform, by adding sodium carbonate to pH=9. The mixture is extracted and left to separate out and the chloroform phase is washed with water, dried and concentrated. The resulting oil is taken up in diethyl ether. A white precipitate forms, which is dried in vacuo at 60° C. over P$_2$O$_5$.

Melting point=178°–179° C.

The following Table, referring to general formula I, discloses compounds of the invention which have been prepared by the procedure of the foregoing Examples.

TABLE

| Compound | n | X | Y | Melting point (°C.) | |
|---|---|---|---|---|---|
| 1 | 1 | 4-Cl | H | 165–166 | hydrochloride |
|   |   |   |   | 172–173.5 | base |
| 2 | 1 | 4-CH$_3$O | H | 177–178 | base |
| 3 | 1 | H | H | 176–177 | base |
| 4 | 1 | 3,4-Cl$_2$ | H | 183–184 | base methane-|

TABLE-continued

| Compound | n | X | Y | Melting point (°C.) | |
|---|---|---|---|---|---|
| | | | | 144–145 | sulphonate |
| 5 | 1 | 4-Cl | 4-Cl | 171–172 | base |
| 6 | 1 | 4-CH$_3$ | H | 164–164.5 | base |
| 7 | 1 | 3-CF$_3$ | H | 161–163 | base |
| 8 | 1 | 2-Cl | H | 173.5–174.5 | hydrobromide |
| | | | | 132.5–134 | base |
| 9 | 1 | H | 2-CH$_3$ | 199–201 | base |
| 10 | 1 | 3-Cl | H | 176–177 | base |
| 11 | 1 | 4-Br | H | 169–170 | base |
| 12 | 1 | 2,4-Cl$_2$ | H | 159–160 | base |
| 13 | 1 | 3-Br | H | 174–175 | base |
| 14 | 1 | H | 4-F | 169–170 | base |
| 15 | 1 | 4-t-C$_4$H$_9$ | H | 192–193 | base |
| 16 | 2 | 2-n-C$_3$H$_7$O | H | 167–168 | base |
| 17 | 2 | 2-Cl | H | 205–206 | hydrobromide |
| 18 | 2 | 2,4-Cl$_2$ | H | 178–179 | base |
| 19 | 2 | 4-Br | H | 175.5–177 | base |
| 20 | 2 | 3-Br | H | 166–167 | base |
| 21 | 2 | H | 4-F | 128–129 | base |
| 22 | 2 | 2-CH$_3$ | 2-CH$_3$O | 165–166 | base |
| 23 | 2 | 3-Cl | H | 148–150 | base |
| 24 | 2 | 4-t-C$_4$H$_9$ | H | 177–178 | base |
| 25 | 2 | 4-n-C$_4$H$_9$O | H | 118–120 | base |

The thiazole derivatives of the present invention were subjected to pharmacological experiments which demonstrated their antidepressant action.

The toxicity of the compounds was determined on mice by intraperitoneal administration. The LD 50 varies from 50 to more than 1000 mg/kg.

The antidepressant action was determined in accordance with the test for the antagonism towards the ptosis caused by reserpine (C. Gouret et al., J. Pharmacol. (Paris), 8, 333–350 (1977)).

The mice (male, CD1 Charles River, France, 18–22 g) simultaneously receive the products to be studied or the solvent (administered intraperitoneally), and the reserpine (4 mg/kg, administered subcutaneously).

After sixty minutes, the degree of palpebral ptosis is estimated for each mouse by means of a rating scale (0 to 4).

The average rating and the percentage variation relative to the control batch are calculated for each dose.

The AD 50, that is to say the dose which reduces the mean ptosis score by 50%, relative to the controls, is determined graphically for each product.

The AD 50 varies from 0.2 to 10 mg/kg, administered intraperitoneally.

Furthermore, the action of the drugs on the ponto-geniculo-occipital points during the reserpine syndrome was studied on curarised rats in order to demonstrate the antidepressant properties of the compounds.

In cats, a specific activity is recorded at the level of the pons, the lateral geniculate nucleus and the occipital cortex, and this activity has been referred to as the ponto-geniculo-occipital (P.G.O.) points.

This spontaneous activity (P.G.O. points) appearing during the wake-sleep cycle can be induced by reserpine, which is a pharmacological agent for reducing the level of the cerebral monoamines.

This electroencephalographic activity, which is modified by neuronal mechanisms under the control of synaptic neurotransmitters, thus constitutes a pharmacological test for studying the central action of the drugs.

All the experiments are carried out by acute treatment on cats of both sexes, weighing 2 to 3 kg.

Before the start of the surgical preparation carried out under ether narcosis, the animal receives an intraperitoneal injection of 0.75 mg/kg of reserpine.

The cat is intubated in order to permit artificial respiration.

A local anaesthetic (2% xylocaine solution) is injected at the pressure points and the incisions.

Cannulas are placed in the femoral vein for the injection of the products and the infusion of a curarising agent, namely gallamine triethiodide (Flaxedril ®), and in the femoral artery for recording the blood pressure.

Monopolar electrodes are screwed at the level of the cortex and coaxial bipolar electrodes are placed stereotactically at the level of the lateral geniculate nuclei.

The curarised animal under artificial respiration is kept at constant temperature throughout the experiment.

The electroencephalogram, the electrocardiogram and the blood pressure are recorded using a model 79 D Grass polygraph.

Increasing doses (0.1, 0.3, 1, 10 and 30 mg/kg) of the products to be studied are injected intravenously every 30 minutes, 4 hours 30 minutes after the administration of the reserpine.

The number of P.G.O. points is automatically counted at 10-minute intervals and expressed as a percentage at 30 minute intervals, the value obtained during the 30 minute control period being taken as the reference (100%).

The effective dose which reduces the number of P.G.O. points by 50% (ED 50) is calculated with the aid of a semi-logarithmic regression curve.

The results are as follows: the ED 50 ranges from 0.2 to 3 mg/kg.

The pharmacological results show that the thiazole derivatives of the present invention can be useful for the treatment of depression.

The compounds of the present invention can be presented in any pharmacological composition form which is suitable for oral or parenteral administration, for example of the form of tablets, coated tablets, gelatin-coated tablets, solutions to be taken orally or injectable solutions in association with any suitable excipient.

The daily posology can range from 5 to 200 mg.

I claim:

1. A thiazole derivative of the formula:

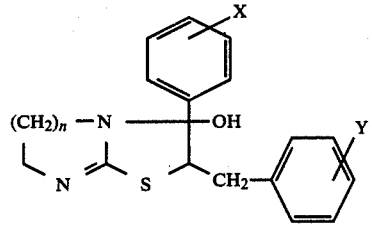

wherein n represents 1 or 2 and each of X and Y independently of one another represents one or more substituents selected from hydrogen and halogen atoms, the trifluoromethyl radical and straight- or branched-chain alkyl and alkoxy radicals of one to four carbon atoms, and pharmaceutically acceptable acid addition salts thereof.

2. A thiazole compound according to claim 1 wherein n represents 1.

3. A thiazole compound according to claim 1 wherein n represents 2.

4. A thiazole compound according to claim 2 wherein each of X and Y independently of one another represents one or more hydrogen or halogen atoms, or trifluoromethyl, methyl, tert.-butyl or methoxy radicals.

5. A thiazole compound according to claim 3 wherein each of X and Y independently of one another represents one or more hydrogen or halogen atoms, or methyl, methoxy, tert.-butyl, n-butoxy or n-propoxy radicals.

6. The thiazole derivative according to claim 1 which is 2-benzyl-3-(3,4-dichlorophenyl)-2,3,5,6-tetrahydroimidazo[2,1-b]thiazol-3-ol, and non-toxic pharmaceutically acceptable acid addition salts thereof.

7. The thiazole derivative according to claim 1 which is 2-benzyl-3-(4-bromophenyl)-2,3,5,6-tetrahydroimidazo[2,1-b]thiazol-3-ol, and non-toxic pharmaceutically acceptable acid addition salts thereof.

8. A method for the treatment of depression which comprises administring to a patient suffering therefrom an effective amount of a thiazole derivative of the formula depicted in claim 1, wherein n, X and Y are as defined in claim 1, or of a non-toxic pharmaceutically acceptable acid addition salt thereof.

9. An antidepressant pharmaceutical composition containing a dose effective as antidepressant of a compound of the formula:

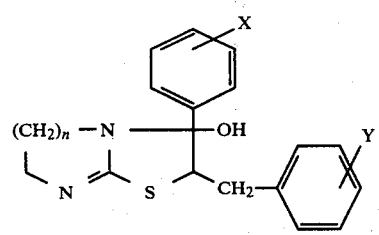

wherein n represents 1 or 2 and each of X and Y independently of one another represents one or more substituents selected from hydrogen and halogen atoms, the trifluoromethyl radical and straight- or branched-chain alkyl and alkoxy radicals of one to four carbon atoms or a non-toxic pharmaceutically acceptable acid addition salt thereof, and a suitable pharmaceutical excepient.

* * * * *